(12) United States Patent
Hively

(10) Patent No.: US 8,065,529 B2
(45) Date of Patent: Nov. 22, 2011

(54) METHODS FOR USING A BIOMETRIC PARAMETER IN THE IDENTIFICATION OF PERSONS

(75) Inventor: Lee M. Hively, Philadelphia, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1185 days.

(21) Appl. No.: 11/804,966

(22) Filed: May 21, 2007

(65) Prior Publication Data

US 2008/0294907 A1 Nov. 27, 2008

(51) Int. Cl.
 *G06F 21/00* (2006.01)
 *G06F 21/06* (2006.01)
 *G06F 21/20* (2006.01)

(52) U.S. Cl. ........ 713/186; 713/182; 713/184; 713/185; 382/115; 382/100; 382/207; 382/189; 726/2; 726/16; 726/17; 726/21; 726/4

(58) Field of Classification Search ..................... None
 See application file for complete search history.

(56) References Cited

U.S. PATENT DOCUMENTS

| | | | | |
|---|---|---|---|---|
| 5,137,027 A | * | 8/1992 | Rosenfeld | 600/544 |
| 5,325,862 A | * | 7/1994 | Lewis et al. | 600/544 |
| 5,626,145 A | * | 5/1997 | Clapp et al. | 600/544 |
| 5,762,611 A | * | 6/1998 | Lewis et al. | 600/544 |
| 5,857,978 A | | 1/1999 | Hively et al. | |
| 6,484,132 B1 | | 11/2002 | Hively et al. | |
| 6,898,299 B1 | * | 5/2005 | Brooks | 382/115 |
| 7,127,283 B2 | * | 10/2006 | Kageyama | 600/544 |
| 7,139,677 B2 | | 11/2006 | Hively et al. | |
| 7,209,861 B2 | * | 4/2007 | Hively | 702/183 |
| 7,249,263 B2 | * | 7/2007 | Chaudhari et al. | 713/186 |
| 7,461,264 B2 | * | 12/2008 | Chen | 713/182 |
| 7,594,122 B2 | * | 9/2009 | Milgramm et al. | 713/186 |
| 2004/0097824 A1 | * | 5/2004 | Kageyama | 600/544 |
| 2005/0017870 A1 | * | 1/2005 | Allison et al. | 340/825.19 |
| 2005/0022034 A1 | * | 1/2005 | Chaudhari et al. | 713/202 |
| 2006/0140484 A1 | * | 6/2006 | Okochi | 382/207 |
| 2006/0215883 A1 | * | 9/2006 | Kim et al. | 382/115 |
| 2007/0049844 A1 | * | 3/2007 | Rosenfeld | 600/544 |
| 2008/0005578 A1 | * | 1/2008 | Shafir | 713/186 |

FOREIGN PATENT DOCUMENTS

JP  2004-248714 A2  9/2004

OTHER PUBLICATIONS

Single trial analysis on EEG signatures to identify individuals Hema, C.R.; Osman, A.A. Signal Processing and Its Applications (CSPA), 2010 6th International Colloquium on (978-1-4244-7121-8) 2010. p. 1-3.*

(Continued)

*Primary Examiner* — Syed A. Zia
(74) *Attorney, Agent, or Firm* — Boyle Fredrickson, SC

(57) ABSTRACT

Brain waves are used as a biometric parameter to provide for authentication and identification of personnel. The brain waves are sampled using EEG equipment and are processed using phase-space distribution functions to compare digital signature data from enrollment of authorized individuals to data taken from a test subject to determine if the data from the test subject matches the signature data to a degree to support positive identification.

13 Claims, 3 Drawing Sheets

OTHER PUBLICATIONS

Sebastien Marcel et al: "Person Authentication Using Brainwaves (EEG) and Maximum A Posteriori Model Adaptation", IEEE Transactions on Pattern Analysis and Machine Intelligence, IEEE Service Center, Los Alamitos, CA, US, vol. 29, No. 4, Apr. 1, 2007, pp. 743-752, XP011168511 ISSN: 0162-8828.

Poulos M et al: "On the Use of EEG Features Towards Person Identification Via Neural Networks," Medical Informatics and the Internet in Medicine, Taylor and Francis, London, GB, vol. 26, No. 1, Jan. 1, 2001; pp. 35-48, XP008035802 ISSN: 1463-9238.

\* cited by examiner

METHODS FOR USING A BIOMETRIC PARAMETER IN THE IDENTIFICATION OF PERSONS

STATEMENT REGARDING FEDERALLY SPONSORED RESEARCH

This invention was made with assistance under Contract No. DE-AC05-00OR22725 with the U.S. Department of Energy. The Government has certain rights in this invention.

BACKGROUND OF THE INVENTION

The field of the invention is identification of persons using biometric parameters.

A biometric parameter of humans is needed to positively identify trusted persons. The typical biometric features include body odor, body salinity, ear pattern, facial recognition, fingernail bed, fingerprints, hand geometry, hand grip, infrared fingertip image, keystroke dynamics, hand vasculature, eye iris and retina, (walking) gait, written signature, voice, and facial thermogram. The attributes of a biometric identity parameter are: security of the factor, protection of individual privacy, compliance with government standards for reliability and accuracy, and adaptability to regional, state, and local requirements. The objectives of personal identification are to deter identity deception and to accelerate recognition of trusted personnel (e.g., authorized firearm carriers in air travel, state/regional/local officials, and trusted insiders in critical infrastructure areas). Other biometric features include: universality—how commonly the biometric is found in each person; uniqueness—how accurately the biometric distinguishes one person from the other; permanence—how well the biometric resists the effects of aging; collectability—how easily the biometric is acquired for processing; performance—achievable accuracy, speed and robustness of the biometric; acceptability—public acceptance of the technology in their daily lives; circumvention—difficulty to circumvent or fool the system into accepting an impostor.

Authentication should require that the subject person be screened in a live setting, as opposed to reviewing records that can be forged, or reviewing passive biometric identifiers that can be extracted from someone who is uncooperative, unaware, or even deceased.

SUMMARY OF THE INVENTION

The present invention improves on prior disclosed biometric methods by providing for identification of test subjects using the sensing of brain waves. The invention provides for a novel method for using brain wave data for positive identification or non-identification of a test subject.

The data is acquired from a known person and converted into at least one enrollment signature in the form of a phase-space distribution function. Data is then acquired to create another a test signature from different scalp data from an unknown test subject. The enrollment signature is compared to the test signature via at least one phase-space dissimilarity measure (PSDM) for either one of a connected phase space or a non-connected phase space. If the test signature is the same as the enrollment signature (at least one PSDM is less than some threshold), the identification of the test subject is confirmed as being the same as the known person, corresponding to the enrollment signature. If the test signature is different (at least one PSDM is greater than this same threshold) from the enrollment signature the identification fails. The PSDM analysis approach was previously disclosed by Hively et al., U.S. Pat. No. 6,484,132, issued 19 Nov. 2002.

The invention therefore provides two functions: 1) authentication (verification that the test and enrollment signatures are the same for allowance of trusted access), and 2) identification (determination that enrollment signature X is the same as test signature Y for identification of a person among others).

The measures of performance are the rate of true positives (correctly identifying same person in the enrollment and test data), and true negatives (correctly rejecting an impostor) as a way of improving the analysis used in the steps outlined above, as further disclosed in Hively, U.S. Pat. No. 7,139,677, issued Nov. 21, 2006.

The invention further provides methods for processing data to provide positive identification of a person, which involve statistical methods utilized by the inventor for monitoring patients to provide forewarning of critical events. In these methods, more that one channel may be sampled (for example, $e_i(1)$ and $e_i(2)$ from channels 1 and two at time $t_i$) and difference data may be used from two channels (for example, $d_i = e_i(1) - e_i(2)$) for both the signature and the test data.

The invention also involves identification of features for "good" and "bad" pass codes or alternative cognitive tasks while the EEG data are acquired, for robustness and reliability that is necessary for real-life applications.

Other objects and advantages of the invention, besides those discussed above, will be apparent to those of ordinary skill in the art from the description of the preferred embodiment, which follows. In the description, reference is made to the accompanying drawings, which form a part hereof, and which illustrate one example of the invention. Such example, however, is not exhaustive of the various embodiments of the invention, and therefore reference is made to the claims, which follow the description for determining the scope of the invention.

DETAILED DESCRIPTION OF THE PREFERRED EMBODIMENT

Figure 1:
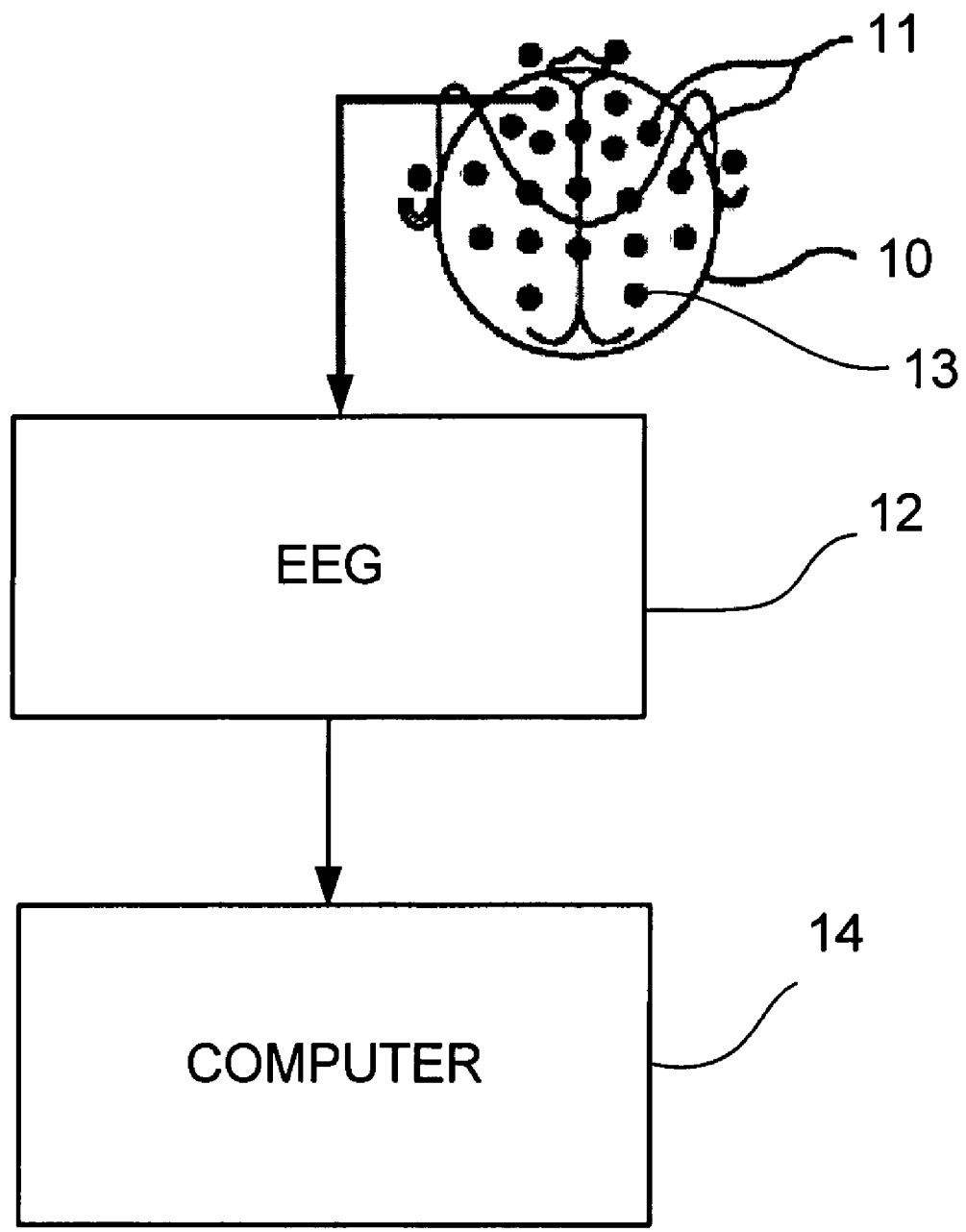
FIG. 1 is apparatus for capturing and processing brain wave data.

FIG. 1 shows apparatus for capturing and processing brain wave data. At least two sensors 11 are placed on the head 10 of a human subject at one of a plurality of pairs of possible positions 13. Signals are input to an EEG (electroencephalogram) unit 12 that digitizes the brain wave signals and provides brain wave data, or channel data as it is sometimes referred to, to a computer 14. This EEG unit 12 is connected via a suitable interface of type known in the art to a personal computer 14, which may be a PC running a Windows® operating system. Other platforms such as a personal-digital-assistant-class device, or palmtop computer and other operating systems can also be used provided the programs described herein are made compatible with such systems.

Figure 2:
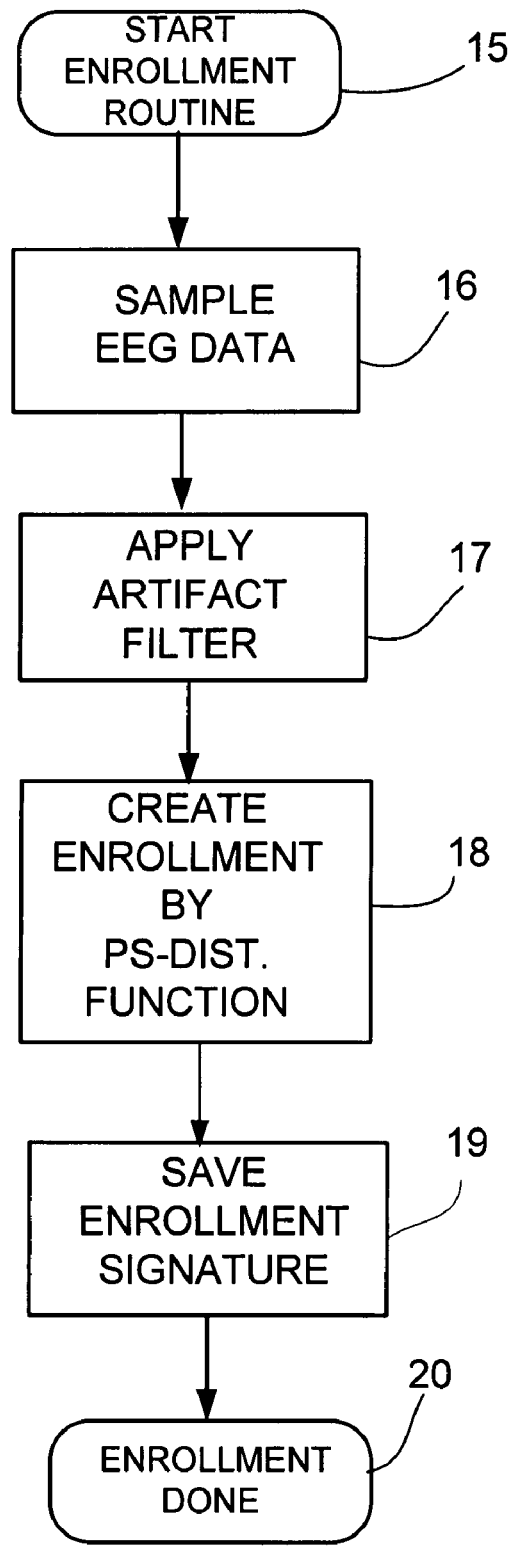
FIG. 2 is a flow chart of a routine to create a digital enrollment signature from brain wave data captured in FIG. 1.

As seen in FIG. 2, the computer 14 is provided with a program including a plurality of program instructions to carry out the function illustrated in FIG. 2. The collection of instructions shall be referred to as the "Enrollment Routine," however, it should be understood that this is for purposes of illustration, rather than dictating a particular organization of instructions in one routine. The start of the "routine" is represented by executing one or more instructions represented by a start block 15. Then, brain wave data for a person providing a digital signature is acquired in one or more sets from one or more EEG channels through the equipment seen and described in FIG. 1, and this is represented by process block 16. Data quality is checked and any bad data is discarded as described in the inventor's prior patents and publications. Then, instructions represented by process block 17 are executed to apply a zero-phase quadratic filter to filter out confounding artifact data, as is known from prior patents and publications of the inventor including Hively, et al., U.S. Pat. No. 5,626,145, issued May 6, 1997. Then, a time-delay, phase space distribution function is computed from this data to create an enrollment signature of the human subject, as represented by process block 18. The result of this computation is saved as an enrollment digital signature, as represented by process block 19. This completes the enrollment routine, as represented by "done" block 20.

Figure 3:
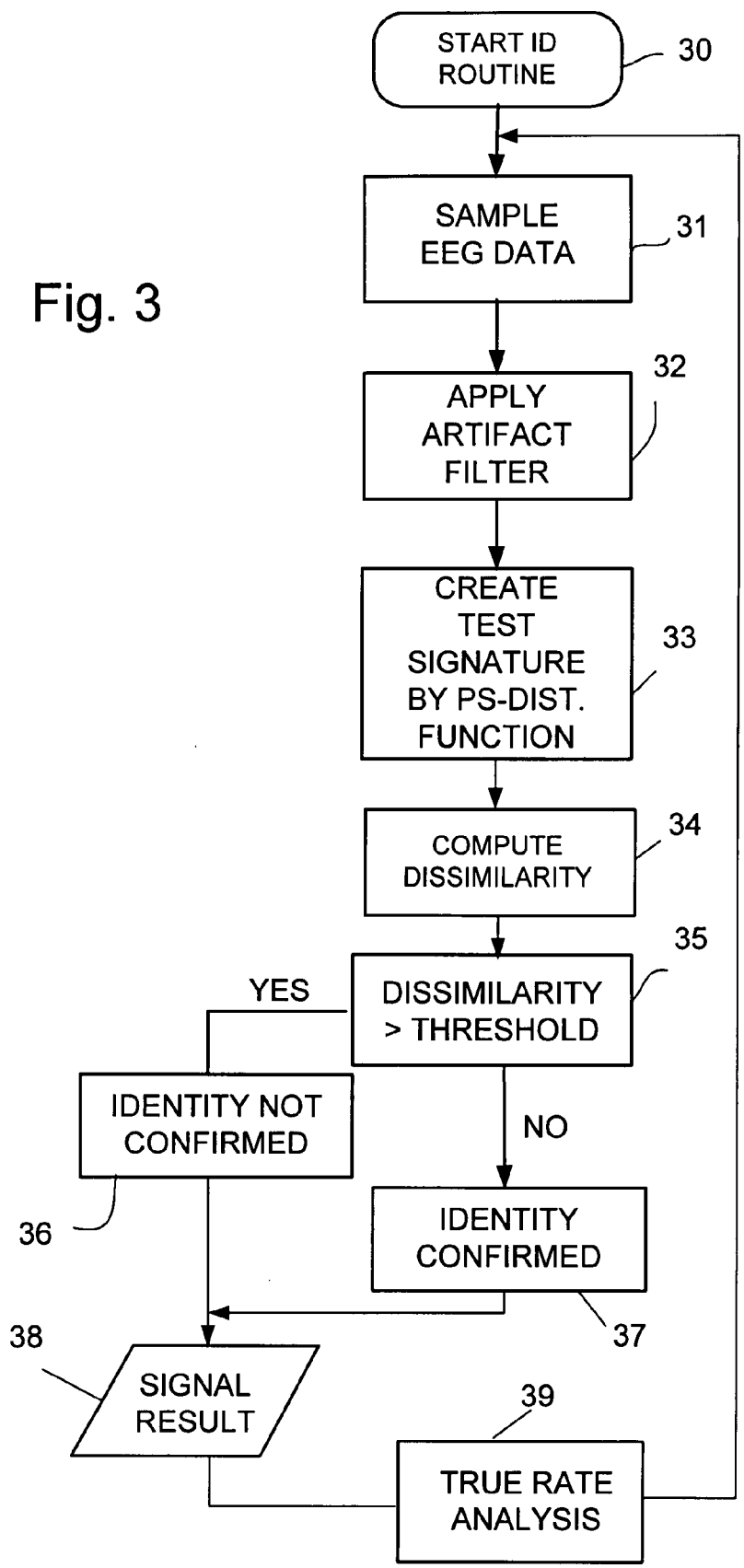
FIG. 3 is a flow chart of a routine to compare data from a test subject to the digital enrollment signature obtained in FIG. 2 in order to make an identity determination of a person.

When wishing to test a subject to see if their data will match a prior signature stored in memory, the routine represented in FIG. 3 is carried out through executing computer program instructions. The beginning of the process, which shall be referred to as the "ID Routine" is represented by start block 30. This is again stated for illustration purposes only and is not intended to limit any particular organization of the program instructions or functions described herein except as necessary to carry out the described method. Again, brain wave data for the test subject is acquired in one or more sets from one or more EEG channels through the equipment seen and described in FIG. 1, and this is represented by process block 31. Data quality is again checked and bad data is discarded. Then, instructions represented by process block 32 are executed to apply a zero-phase quadratic filter to remove confounding artifact data, as described earlier for the subject providing the signature. Next, a time-delay, phase space distribution function is computed for the test subject for each respective channel of data, as represented by process block 33, to create the test signature.

As represented by block 34, at least one measure of dissimilarity is computed, as disclosed by Hively et al. in U.S. Pat. No. 6,484,132, issued Nov. 19, 2002, for measuring the dissimilarity between the enrollment signature and the test signature. This measure of dissimilarity may be raw, normalized by a factor of ½N or renormalized.

As represented by decision block 35, at least one measure of dissimilarity is compared to a threshold ($U_C$). Detection of dissimilarity between the enrollment and test signatures for either one PSDM, or a plurality ($N_{SIM}$) of renormalized PSDMs, greater than the threshold, leads to non-confirmation of the person's identity as represented by process block 36. Detection of a small dissimilarity less than the threshold or no dissimilarity between the enrollment and test signatures for one PSDM, or a plurality ($N_{SIM}$) of renormalized PSDMs, results in confirmation of a person's identity, as represented by process block 37. The result is then signaled to a human observer through a visual display, an audible sound, or other human/machine interface methods known in the art, as represented by I/O block 38.

As a further step in the analysis, represented by process block 39, the program maximizes the rate of true positives, plus true negatives, as disclosed by Hively, U.S. Pat. No. 7,139,677, issued Nov. 21, 2006, and U.S. Pat. No. 7,209,861, issued Apr. 24, 2007 on the basis of characterizations of at least two known enrollment signatures and two known test signatures.

In the aforementioned process, one or more biometric parameters for which data is to be analyzed, can be selected such that one data channel can be used in place of multiple data channels without sacrificing consistent positive results. An example of such a parameter is a difference computation for two preferred channels of electroencephalogram (EEG) data. This approach allows for construction of phase-space dissimilarity measures (PSDM) from multiple channels using the fusion of multiple time-serial data channels into a multi-channel time-delay phase-space (PS) reconstruction as disclosed by Hively in U.S. Pat. No. 7,209,861, issued Apr. 24, 2007.

This has been a description of one detailed example of the invention. It will apparent to those of ordinary skill in the art that certain modifications might be made without departing from the scope of the invention, which is defined by the following claims.

I claim:

1. A method for processing data to provide positive identification of a person, comprising:
    acquiring a plurality of sets of data for at least one channel of human brain wave data from at least one first person for the purpose of providing an enrollment signature;
    acquiring a plurality of sets of data for at least one channel of human brain wave data from at least one second person for the purpose of providing a test signature;
    computing at least one measure of dissimilarity between the enrollment signature and the test signature for distribution functions derived from at least one of a connected phase space and a non-connected phase space;
    comparing said measure of dissimilarity to a threshold in which exceeding the threshold results in non-confirmation of an identity of the second person being also an identity of the first person and in which not exceeding the threshold results in confirmation of the identity of the second person being also the identity of the first person; and
    signaling an observer that the second person's identity has either been confirmed or not confirmed.

2. The method of claim 1, further comprising:
    determining true positive indications for confirming the second person's identity for each channel of data in the plurality of sets of data;
    calculating a true positive indication rate for confirming the second person's identity for each channel of data; and
    comparing true positive indication rates for respective channels to determine at least one channel with a greatest channel-consistent total-true rate in said at least one channel.

3. The method of claim 1, further comprising:
    determining true negative indications for not confirming the second person's identity for each channel of data in the plurality of sets of data;
    calculating a true negative indication rate for not confirming the second person's identity for each channel of data; and
    comparing true negative indication rates for respective channels to determine at least one channel with a greatest channel-consistent true negative indication rate in said at least one channel.

4. The method of claim 1, wherein the second person is a live and present human being.

5. The method of claim 1, wherein the brain wave data comprises at least one channel of EEG data that is analyzed to create the enrollment signature of the first person and at least one channel of EEG data that is analyzed to represent the second person.

6. The method of claim 1, further comprising filtering out confounding artifact data from the plurality of sets of data before computing the connected phase space for the channel data.

7. A method for new use of brain wave data, the method comprising:
   computing a measure of dissimilarity for at least one distribution function derived from at least one of a connected phase space and a non-connected phase space for brain wave data providing an enrollment signature for a known human person and for brain wave data providing a test signature from a test human person;
   comparing said measure of dissimilarity to a threshold in which exceeding the threshold results in non-confirmation of a test human person's identity being that of the known human person and in which not exceeding the threshold results in confirmation of the test human person's identity being that of the known human person; and
   signaling an observer that the test subject's identity has either been confirmed or not confirmed.

8. The method of claim 7, further comprising:
   determining true positive indications of condition change for confirming the test human person's identity for each channel of data in a plurality of sets of data;
   calculating a true positive indication rate for confirming the test human person's identity for each channel of data; and
   comparing true positive indication rates for respective channels to determine at least one channel with a greatest channel-consistent true rate in said at least one channel.

9. The method of claim 7, further comprising:
   determining true negative indications of condition change for not confirming the test human person's identity for each channel of data in the plurality of sets of data;
   calculating a true negative indication rate for not confirming the test human person's identity for each channel of data; and
   comparing true negative indication rates for respective channels to determine at least one channel with a greatest channel-consistent true negative indication rate in said at least one channel.

10. The method of claim 7, wherein the test human person is provided by a live and present human being.

11. The method of claim 7, wherein the brain wave data comprises at least one channel of EEG data that is analyzed to create the enrollment signature for the known human person and at least one channel of data that is analyzed to represent the test human person.

12. The method of claim 7, further comprising
   acquiring a plurality of sets of data for at least one channel of human brain wave from at least one known human person for a purpose of providing the enrollment signature for the known human person;
   acquiring a plurality of sets of data for at least one channel of human brain wave data from at least one test human person for a purpose of providing the test signature.

13. The method of claim 7, further comprising filtering out confounding artifact data from the brain wave data.

* * * * *